United States Patent
Tai et al.

(10) Patent No.: US 9,366,627 B2
(45) Date of Patent: Jun. 14, 2016

(54) LIGHT TRANSMITTANCE MEASURING APPARATUS

(71) Applicant: TPK TOUCH SOLUTIONS (XIAMEN) INC., Xiamen (CN)

(72) Inventors: Chung-Hang Tai, Hsinchu (TW); Lijun Li, Xiamen (CN); Musheng Li, Zhangzhou (CN); Xinfa Chen, Quanzhou (CN); Meishu Wang, Xiamen (CN)

(73) Assignee: TPK Touch Solutions (Xiamen) Inc., Xiamen (CN)

( * ) Notice: Subject to any disclaimer, the term of this patent is extended or adjusted under 35 U.S.C. 154(b) by 0 days.

(21) Appl. No.: 14/572,806

(22) Filed: Dec. 17, 2014

(65) Prior Publication Data

US 2015/0204783 A1 Jul. 23, 2015

(30) Foreign Application Priority Data

Jan. 17, 2014 (CN) .......................... 2014 1 0020634

(51) Int. Cl.
*G01N 21/59* (2006.01)

(52) U.S. Cl.
CPC ...................................... *G01N 21/59* (2013.01)

(58) Field of Classification Search
CPC ... G01N 21/256; G01N 21/534; G01N 21/59; G01N 21/3151; G01N 2021/3155; G01N 1/40; G01J 3/42
USPC .................................................. 356/432–440
See application file for complete search history.

(56) References Cited

U.S. PATENT DOCUMENTS

| | | | | |
|---|---|---|---|---|
| 3,765,775 A * | 10/1973 | Ganssle | .................... | G01J 3/51 356/244 |
| 5,696,580 A * | 12/1997 | Kubo | .................. | G01N 21/4133 356/128 |
| 2003/0025909 A1* | 2/2003 | Hallstadius | ............. | A23L 3/003 356/436 |
| 2008/0144005 A1* | 6/2008 | Guiney | .............. | G01N 21/3151 356/39 |
| 2010/0053621 A1* | 3/2010 | Olson | ..................... | A61L 2/208 356/437 |
| 2011/0101226 A1* | 5/2011 | Ben-Zvi | ............... | G01N 21/958 250/358.1 |
| 2014/0163387 A1* | 6/2014 | Kang | .................. | A61B 5/7225 600/476 |

FOREIGN PATENT DOCUMENTS

WO   WO 2013/143859   * 10/2013

* cited by examiner

*Primary Examiner* — Hoa Pham
(74) *Attorney, Agent, or Firm* — Gokalp Bayramoglu

(57) ABSTRACT

A light transmittance measuring apparatus includes a housing made of opaque material, a light source device disposed in the housing and for emitting a first light beam and a second light beam to the object, a light sensor and a microcontroller. The first light beam and the second light beam have different wavelength ranges and have a first light intensity value and a second light intensity value, respectively. The light sensor is for sensing the first and second light beams after passing through the object and obtaining a third and fourth light intensity values, respectively. The microcontroller is for comparing the first and third light intensity values to obtain the light transmittance of the object under the first light beam and compare the second and fourth light intensity values to obtain the light transmittance of the object under the second light beam.

20 Claims, 8 Drawing Sheets

LIGHT TRANSMITTANCE MEASURING APPARATUS

BACKGROUND OF THE INVENTION

This application claims priority to Chinese Application Serial Number 201410020634.3, filed on Jan. 17, 2014, which is herein incorporated by reference.

FIELD OF THE INVENTION

The present invention relates to a light transmittance measuring apparatus, and more particularly to a light transmittance measuring apparatus used to measure a light transmittance of an object to be tested.

BACKGROUND OF THE INVENTION

Basically, the smart phones in market are equipped with a light sensor, for automatically adjusting a screen's brightness, and a proximity sensor, for sensing the distance between a user's face and the screen while the user is making a phone call through the smart phone. Thus, through the employment of light sensor and a proximity sensor, smart phone can automatically turn off the screen thereof while the user is using the smart phone for talking and thereby prevent misoperations while the user's face is touching to the screen. In addition, it is understood that tablet or e-book may be also equipped with the light sensor.

In addition, smart phones are also equipped with a protective glass having a hole structure. The hole structure is designed for receiving a specific range of wavelength and having a specific light transmittance based on the models or specifications of the employed light sensor and proximity sensor. In other words, the performances of light sensor and proximity sensor are directly related to the light transmittance of the hole structure of the protective glass under a specific light beam. Thus, the measurement for determining whether the light transmittance of the hole structure of the protective glass under a specific light beam (for example, visible light and near-infrared light) is qualified or not is particularly important.

However, the existing light transmittance measuring apparatuses have lower measurement accuracy due to are designed without considering much about the impact of external ambient light. In addition, the existing light transmittance measuring apparatuses have a lower production efficiency due to unable to measure the light transmittances of the hole structure of protective glass under two light beams with different wavelength ranges (for example, the green light and the near-infrared light) at the same time; in other words, the two different light beams are needed to be measured individually. Furthermore, the existing light transmittance measuring apparatuses have a lower compatibility due to are customized; in other words, the existing light transmittance measuring apparatuses are needed to be redesigned for another type of object to be tested.

SUMMARY OF THE INVENTION

One object of the present invention is to provide a light transmittance measuring apparatus having simpler operation and higher degree of automation.

The present invention provides a light transmittance measuring apparatus used to measure a light transmittance of an object. The light transmittance measuring apparatus includes a housing, a light source device, a light sensor and a microcontroller. The housing is made of an opaque material. The light source device is disposed in the housing and configured to emit a first light beam and a second light beam to the object. The first light beam and the second light beam have different wavelength ranges and have a first light intensity value and a second light intensity value, respectively. The light sensor is disposed in the housing and configured to sense the first light beam and the second light beam after passing through the object and accordingly obtain a third light intensity value and a fourth light intensity value, respectively. The microcontroller is disposed in the housing and electrically connected to the light source device and the light sensor. The microcontroller is configured to compare the first and third light intensity values and accordingly obtain the light transmittance of the object under the first light beam and compare the second and fourth light intensity values and accordingly obtain the light transmittance of the object under the second light beam.

In one embodiment, the aforementioned light transmittance measuring apparatus further includes a measurement start/stop button disposed on the housing and electrically connected to the microcontroller. The measurement start/stop button is configured to generate a measurement start signal in response to a press of the measurement start/stop button when the housing is in an open state. The microcontroller is further configured to switch the housing from the open state to a close state and control the light source device to sequentially emit the first and second light beams to the object in response to the measurement start signal.

In one embodiment, the aforementioned light source device includes a first light source, a second light source and a rotation mechanism. The first light source is configured to emit the first light beam. The second light source is configured to emit the second light beam. The rotation mechanism is electrically connected to the microcontroller and includes a rotation part, a first connection part and a second connection part. The first and second connection parts both are connected to the rotation part. The rotation mechanism is connected to the first and second light sources through the first and second connection parts, respectively. The microcontroller is further configured to control the rotation part to rotate in response to the measurement start signal and thereby the first and second connection parts drive the first and second light sources to perform a position switch, respectively.

In one embodiment, the aforementioned light transmittance measuring apparatus further includes a movable loading platform disposed in the housing and electrically connected to the microcontroller. The movable loading platform is configured to load the object. The microcontroller is further configured to control the movable loading platform to move between to the light source device and the light sensor in response to the measurement start signal and thereby switch the housing from the open state to the close state.

In one embodiment, the aforementioned microcontroller is further configured to control the movable loading platform to perform a position modulation operation when the movable loading platform is moved between to the light source device and the light sensor and the housing is in the close state.

In one embodiment, the aforementioned measurement start/stop button is further configured to generate a measurement stop signal in response to a press of the measurement start/stop button when the housing is in the close state, wherein the microcontroller is further configured to move the movable loading platform out of the housing in response to the measurement stop signal and thereby switch the housing from the close state to the open state.

In one embodiment, the aforementioned light transmittance measuring apparatus further includes a vacuum suction device disposed in the housing and electrically connected to the microcontroller. The microcontroller is further configured to control the vacuum suction device to generate an air flow in the housing in response to the measurement start signal and thereby form a negative pressure to fix the object to the movable loading platform.

In one embodiment, the aforementioned light transmittance measuring apparatus further includes a display apparatus disposed on the housing and electrically connected to the microcontroller. The display apparatus is configured to show the light transmittances, obtained by the microcontroller, of the object under the first and second light beams.

In one embodiment, the aforementioned light transmittance measuring apparatus further includes a notice device disposed on the housing and electrically connected to the microcontroller. The microcontroller is further configured to control the notice device to issue an alarm signal when the obtained light transmittances of the object under first and second light beams are not qualified.

In one embodiment, the aforementioned display apparatus includes a numeral tube.

In one embodiment, the aforementioned notice device includes an indicator light or a buzzer.

In one embodiment, the aforementioned first light beam is a green light having a wavelength range from 495 nm to 570 nm. The aforementioned second light beam is a near-infrared light having a wavelength range from 750 nm to 1400 nm.

In one embodiment, the aforementioned object is a protective glass comprising at least one hole-shaped region. The first and second light beams emitted from the light source device are configured to sequentially pass through the at least one hole-shaped region of the protective glass.

In summary, because the external ambient light can be completely blocked by the housing in close state, the interference of the ambient light on the object to be tested is efficiently reduced. Thus, the light transmittance measuring apparatus of the present invention has higher measuring accuracy. In addition, because the light source device is able to sequentially emit two light beams with different wavelength ranges and the rotation mechanism is able to switch the two light beams, the measurement of the two different light beams can be completed by one light transmittance measuring apparatus of the present invention. In addition, because the measuring process, from the object to be tested is placed on the movable loading platform to the measuring result is obtained, is automatically controlled by the microcontroller, the measuring time is shorter and an operator can handle more than one light transmittance measuring apparatus of the present invention at the same time. Thus, the light transmittance measuring apparatus of the present invention has higher efficiency and improved production performance. In addition, when the light transmittance measuring apparatus is used for other types of object or other light sources with specific wavelength ranges, only the light source device and the movable loading platform are needed to be changed due to both have the modular design feature. Thus, the light transmittance measuring apparatus of the present invention has a higher compatibility.

BRIEF DESCRIPTION OF THE DRAWINGS

The present invention will become more readily apparent to those ordinarily skilled in the art after reviewing the following detailed description and accompanying drawings, in which.

DETAILED DESCRIPTION OF PREFERRED EMBODIMENTS

The present invention will now be described more specifically with reference to the following embodiments. It is to be noted that the following descriptions of preferred embodiments of this invention are presented herein for purpose of illustration and description only. It is not intended to be exhaustive or to be limited to the precise form disclosed.

Figure 1:
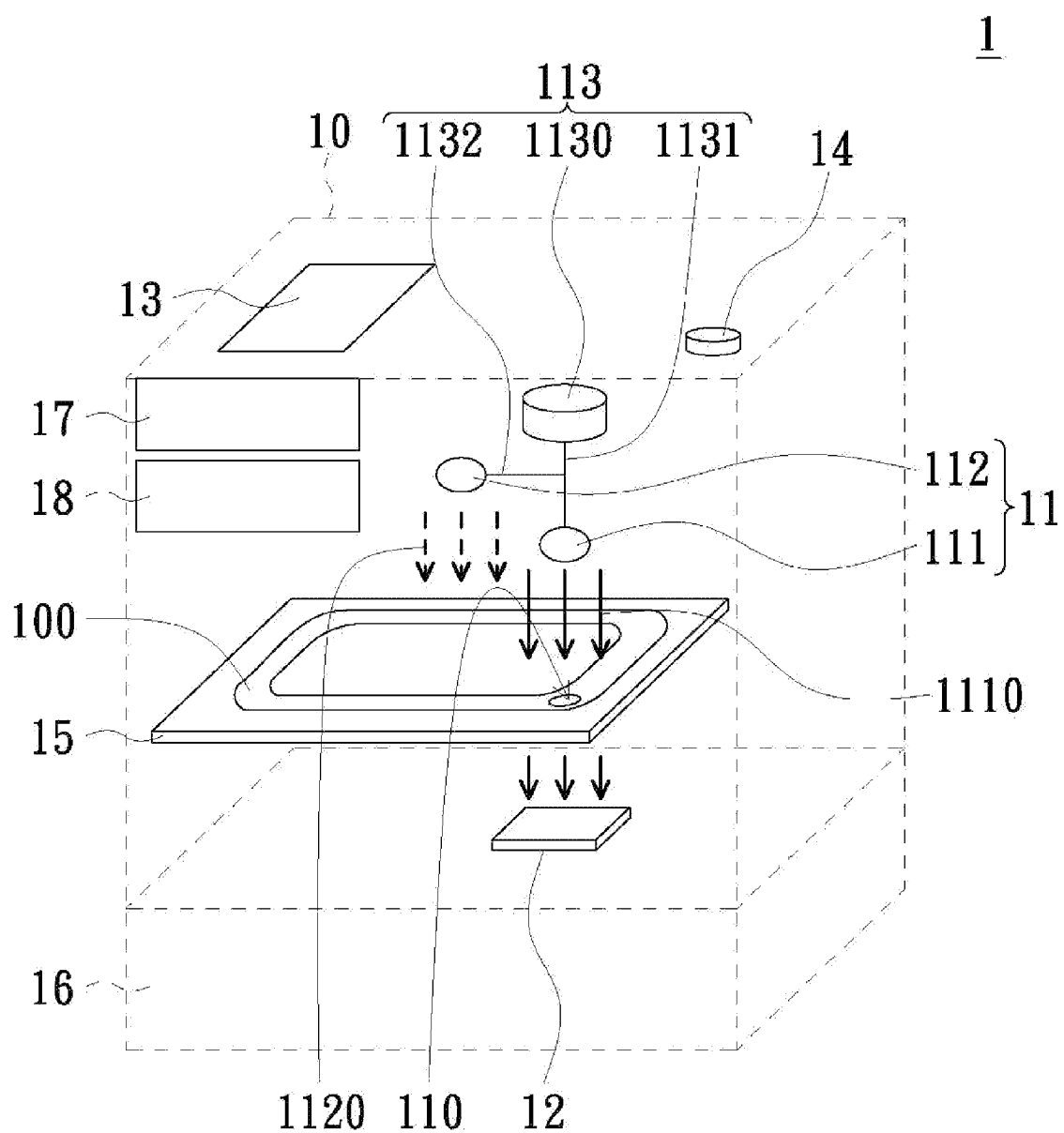
FIG. 1 is a schematic structural view of a light transmittance measuring apparatus in accordance with an embodiment of the present invention.
Figure 2:
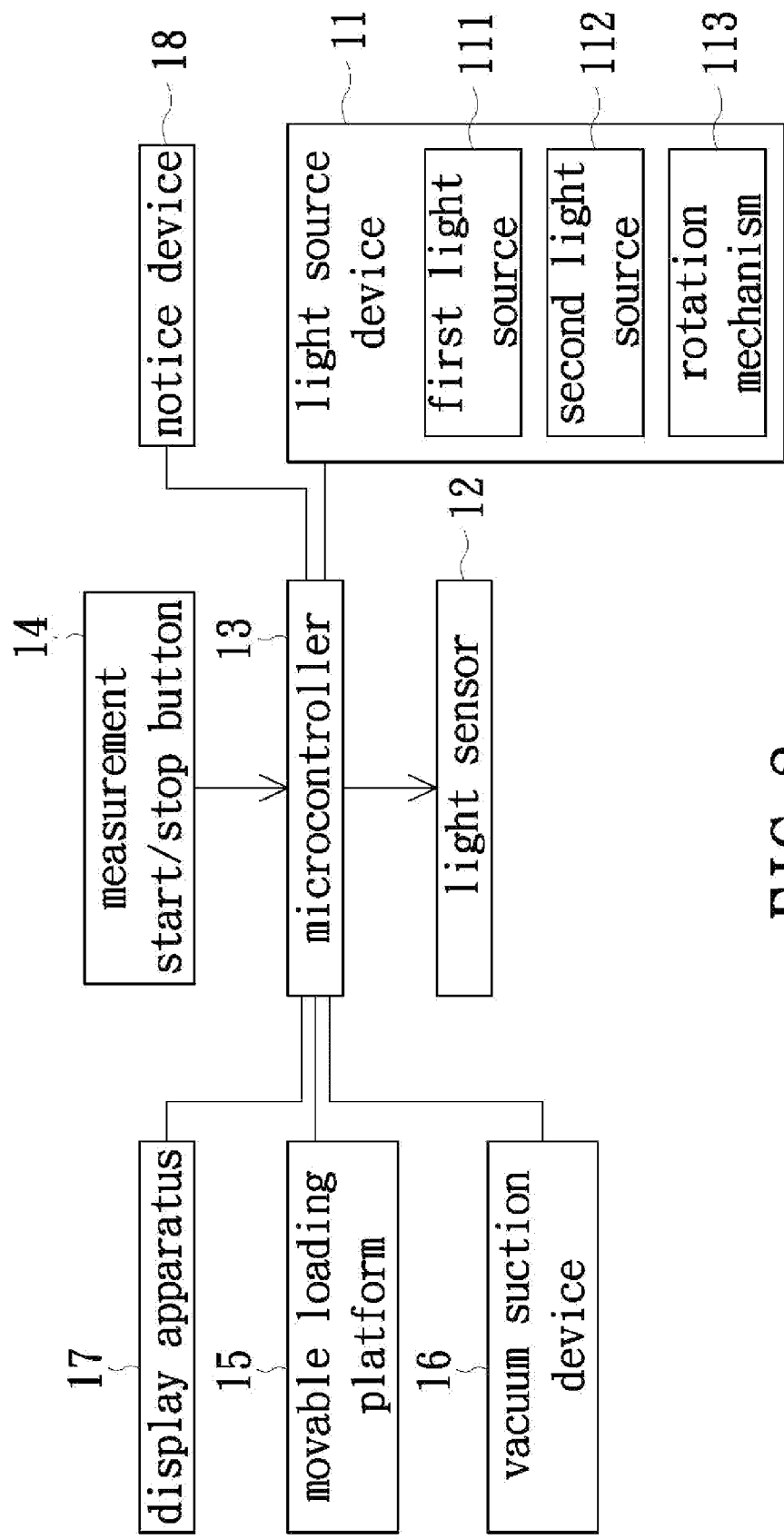
FIG. 2 is a schematic functional block view of the light transmittance measuring apparatus shown in FIG. 1.

FIG. 1 is a schematic structural view of a light transmittance measuring apparatus in accordance with an embodiment of the present invention. FIG. 2 is a schematic functional block view of the light transmittance measuring apparatus shown in FIG. 1. As shown, the light transmittance measuring apparatus 1 in this embodiment is used to measure a light transmittance of an object; wherein the object hereafter may be referred to as a protective glass 100 of smart phone or tablet computer, but the present invention is not limited thereto. The protective glass 100 has at least one hole-shaped region 110, and light transmittance measuring apparatus 1 in this embodiment is exemplarily used to measure the light transmittance of the hole-shaped region 110 of the protective glass 100.

As shown in FIGS. 1 and 2, the light transmittance measuring apparatus 1 in this embodiment includes a housing 10, a light source device 11, a light sensor 12 and a microcontroller 13. The housing 10 is made of opaque material, for example. The light source device 11 is disposed in the housing 10 and includes a first light source 111 and a second light source 112. The first light source 111 is configured to emit a first light beam 1110 and the second light source 112 is configured to emit a second light beam 1120; wherein the first light beam 1110 and the second light beam 1120 have different wavelength ranges. The first light beam 1110 and the second light beam 1120 may be sequentially emitted to the hole-shaped region 110 of the protective glass 100; wherein the first light beam 1110 and the second light beam 1120 originally have a first light intensity value and a second light intensity value, respectively. The light sensor 12 is disposed in the housing 10 and configured to sense the first light beam 1110 and the second light beam 1120 after passing through the hole-shaped region 110; wherein the light sensor 12 may sense that the first light beam 1110 and the second light beam 1120 after passing through the hole-shaped region 110 have a third light intensity value and a fourth light intensity value, respectively. The microcontroller 13 is disposed in the housing 10 and electrically connected to the light source device 11 and the light sensor 12. The microcontroller 13 is configured to compare the first light intensity value and the third light intensity value and accordingly obtain the light transmittance of the hole-shaped region 110 of the protective glass 100 under the first light beam 1110. Similarly, the microcontroller 13 is further configured to compare the second light intensity value and the fourth light intensity value and accordingly obtain the light transmittance of the hole-shaped region 110 of the protective glass 100 under the second light beam 1120. In general, light transmittance may be obtained by the equation: $T=(I_{OUT}/I_{IN})\times100\%$; where $I_{IN}$ is the light intensity value of an incident light (for example, the light intensity values of the first light beam 1110 and the second light beam 1120 before passing through the hole-shaped region 110), and $I_{OUT}$ is the light intensity value of the aforementioned incident light after passing through an object (for example, the light intensity values of the first light beam 1110 and the second light beam 1120 after passing through the hole-shaped region 110). Thus, the light transmittance of the hole-shaped region 110 under the first light beam 1110 is: (the third light intensity value/the first light intensity value)×100%; and the light transmittance of the hole-shaped region 110 under the second light beam 1120 is: (the fourth light intensity value/the second light intensity value)×100%.

In one embodiment, the first light source 111 is configured to emit the first light beam 1110 before the second light source 112 is configured to emit the second light beam 1120; and accordingly, the light transmittance measuring apparatus 1 in the embodiment is configured to measure the light transmittance of the hole-shaped region 110 of the protective glass 100 under the first light beam 1110 first and then measure the light transmittance of the hole-shaped region 110 under the second light beam 1120. In one embodiment, the first light beam 1110 emitted from the first light source 111 is a green light, which has a wavelength range from 495 nm to 570 nm, and the second light beam 1120 emitted from the second light source 112 is a near-infrared light, which has a wavelength range from 750 nm to 1400 nm; however, it is understood that the present invention is not limited thereto and any light source capable of emitting a specific wavelength range of light beam may be employed based on actual needs. In addition, the light transmittance measuring apparatus 1 exemplarily illustrated in FIG. 1 includes two light sources (that is, the first light source 111 and the second light source 112); however, it is understood that the present invention is not limited to the number of light source.

The more-detailed description of the structure of the light transmittance measuring apparatus 1 in this embodiment will be described as follow.

As shown in FIGS. 1 and 2, the light transmittance measuring apparatus 1 in this embodiment may further include a measurement start/stop button 14. The measurement start/stop button 14 is disposed with the housing 10 and electrically connected to the microcontroller 13. In FIG. 1, the measurement start/stop button 14 is exemplarily disposed on the outer surface of the housing 10; however, it is understood that the present invention is not limited thereto. The measurement start/stop button 14 is configured to generate a measurement start signal in response to a press of the measurement start/stop button 14. In one embodiment, the microcontroller 13 is further configured to switch the housing 10 from an open state to a close state and control the first light source 111 and the second light source 112 of the light source device 11 to sequentially emit the first light beam 1110 and the second light beam 1120, respectively, to the hole-shaped region 110 of the protective glass 100 for a light transmittance measurement.

As shown in FIGS. 1 and 2, the light source device 11 in this embodiment may further include a rotation mechanism 113. The rotation mechanism 113 is electrically connected to the microcontroller 13 and includes a rotation part 1130, a first connection part 1131 and a second connection part 1132; wherein the first connection part 1131 and the second connection part 1132 both are connected to the rotation part 1130. In addition, the rotation mechanism 113 is connected to the first light source 111 and the second light source 112 through the first connection part 1131 and the second connection part 1132, respectively. In one embodiment, the microcontroller 13 is further configured to control the rotation part 1130 of the rotation mechanism 113 to rotate in response to the measurement start signal, so that the first connection part 1131 and the second connection part 1132 can drive the first light source 111 and the second light source 112 to perform a position switch, respectively. In other words, once the light transmittance measurement of the hole-shaped region 110 under the first light beam 1110 is completed, the light transmittance measuring apparatus 1 can immediately measure the light transmittance of the hole-shaped region 110 under the second light beam 1120 by switching the positions of the first light source 111 and the second light source 112 through the rotation mechanism 113. It is to be noted that the second light source 112 is turned off when the first light source 111 is being used for the light transmittance measurement; similarly, the first light source 111 is turned off when the second light source 112 is being used for the light transmittance measurement.

As shown in FIGS. 1 and 2, the light transmittance measuring apparatus 1 in this embodiment may further include a movable loading platform 15. The movable loading platform 15 is disposed in the housing 10 and electrically connected to the microcontroller 13. The movable loading platform 15 is configured to load the protective glass 100. In one embodiment, the microcontroller 13 is further configured to control the movable loading platform 15 to move between to the light source device 11 and the light sensor 12 in response to the measurement start signal and thereby switch the housing 10 from the open state to the close state. Because the housing 10 is made of opaque material, the protective glass 100 is prevented from being affected by any external ambient light when the housing 10 is in the close state; and consequentially, the light transmittance measuring apparatus 1 has improved measuring accuracy.

In one embodiment, the microcontroller 13 is further configured to control the movable loading platform 15 to perform a position modulation operation when the movable loading platform 15 is moved between to the light source device 11 and the light sensor 12 and the housing 10 is in the close state. Specifically, by performing the position modulation operation, the hole-shaped region 110 of the protective glass 100 can be accurately aligned to the light source device 11 and the light sensor 12, and consequentially the first light beam 1110 and the second light beam 1120 can accurately pass through the hole-shaped region 110 of the protective glass 100. Thus, the light transmittance measuring apparatus 1 has improved measuring accuracy.

Once the aforementioned light transmittance measurement is completed, the measurement start/stop button 14 is further configured to generate a measurement stop signal in response to another press of the measurement start/stop button 14. In one embodiment, the microcontroller 13 is further configured to move the movable loading platform 15 out of the housing 10 in response to the measurement stop signal and thereby switch the housing 10 from the close state to the open state. Then, another protective glass 100 to be tested can be placed on the movable loading platform 15, and the movable loading platform 15 is moved between to the light source device 11 and the light sensor 12 in response to the measurement start signal resulted by still another press of the measurement start/stop button 14 and thereby switch the housing 10 from the open state to the close state, for another cycle of the light transmittance measurement.

As shown in FIGS. 1 and 2, the light transmittance measuring apparatus 1 in this embodiment may further include a vacuum suction device 16. The vacuum suction device 16 is disposed in the housing 10 and electrically connected to the microcontroller 13. In FIG. 1, the vacuum suction device 16 is exemplarily disposed in the bottom of the housing 10; however, it is understood that the present invention is not limited thereto. In one embodiment, the microcontroller 13 is further configured to control the vacuum suction device 16 to generate an air flow in the housing 10 in response to the measurement start signal so as to form a negative pressure, thereby fix the protective glass 100 to the movable loading platform 15. Thus, the protective glass 100 is prevented from having a displacement on the movable loading platform 15 in the process of light transmittance measurement. Thus, the light transmittance measuring apparatus 1 has improved measuring accuracy.

As shown in FIGS. 1 and 2, the light transmittance measuring apparatus 1 in this embodiment may further include a display apparatus 17. The display apparatus 17 is disposed with the housing 10 and electrically connected to the microcontroller 13. In FIG. 1, the display apparatus 17 is exemplarily disposed on the outer surface of the housing 10; however, it is understood that the present invention is not limited thereto. In one embodiment, the microcontroller 13 is further configured to perform a write-and-display control on the display apparatus 17 via serial peripheral interface (SPI) manner. The display apparatus 17 is configured to display the light transmittances, obtained by the microcontroller 13, of the hole-shaped region 110 of the protective glass 100 under the first light beam 1110 and the second light beam 1120. In one embodiment, the display apparatus 17 is implemented by a numeral tube; however, it is understood that the present invention is not limited thereto.

As shown in FIGS. 1 and 2, the light transmittance measuring apparatus 1 in this embodiment may further include a notice device 18. The notice device 18 is disposed with the housing 10 and electrically connected to the microcontroller 13. In FIG. 1, the notice device 18 is exemplarily disposed on the outer surface of the housing 10; however, it is understood that the present invention is not limited thereto. In one embodiment, the microcontroller 13 is further configured to control the notice device 18 to issue an alarm signal when the light transmittances of the hole-shaped region 110 of the protective glass 100 under the first light beam 1110 and the second light beam 1120 are obtained. In one embodiment, the notice device 18 may be an indicator light or a buzzer; however, it is understood that the present invention is not limited thereto.

Figure 3A:
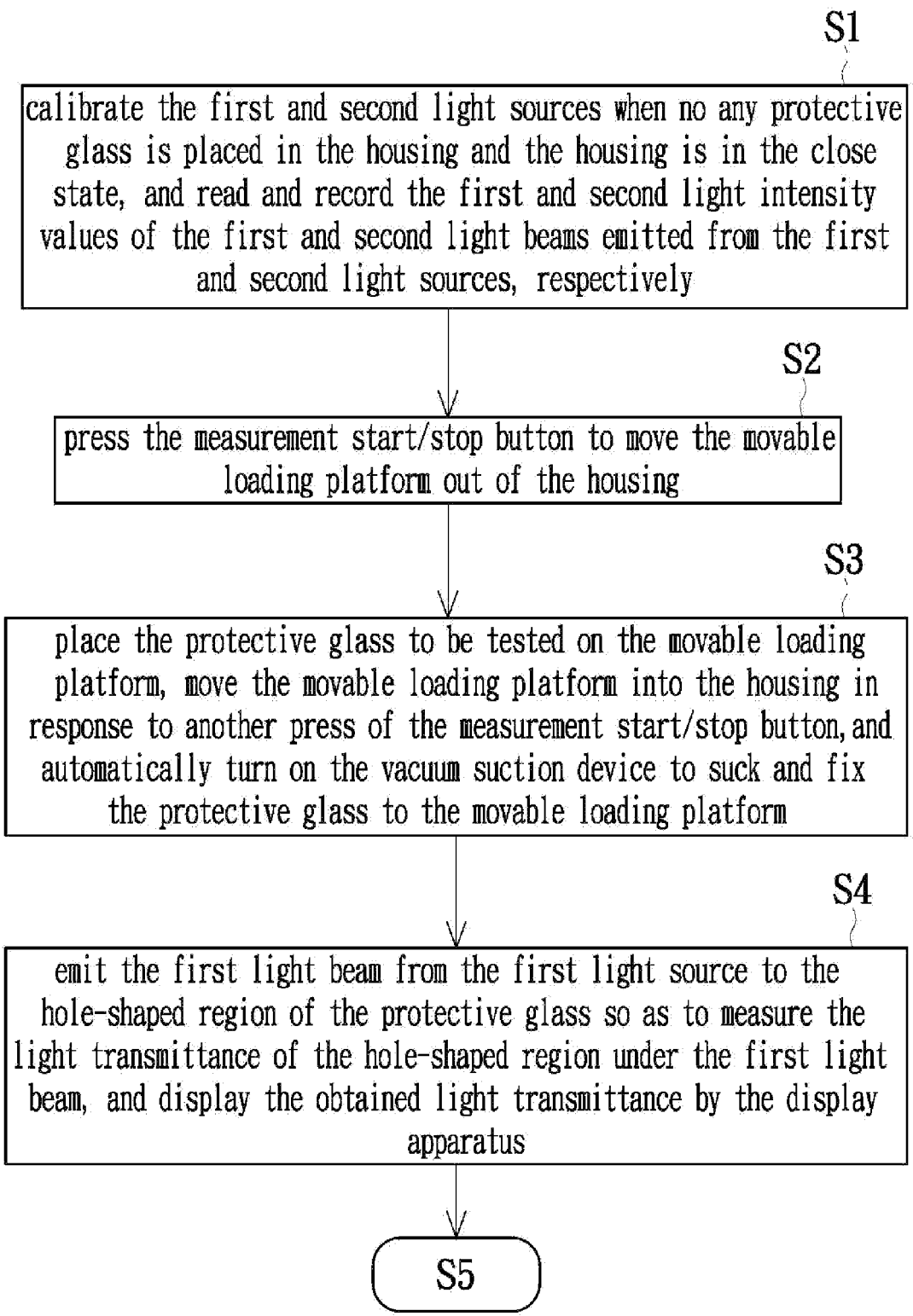
FIGS. 3A and 3B are flowcharts illustrating an operation process of the light transmittance measuring apparatus shown in FIG. 1.
Figure 3B:
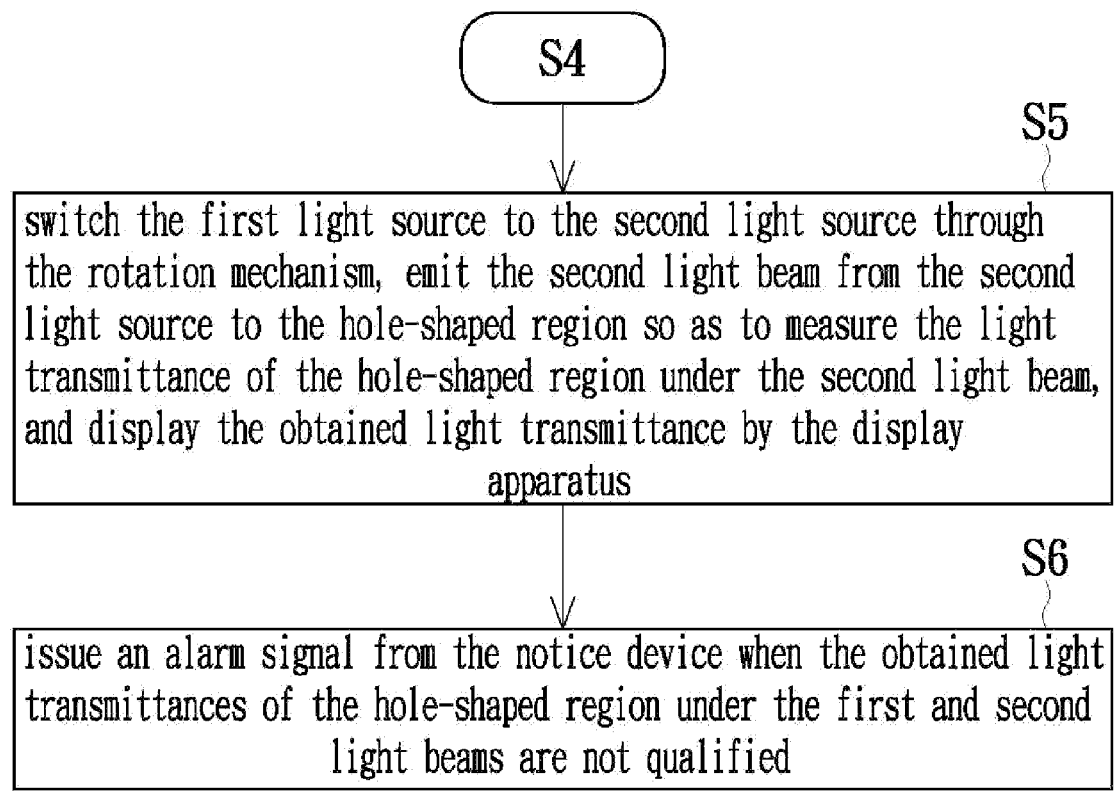

FIGS. 3A and 3B are flowcharts illustrating an operation process of the light transmittance measuring apparatus shown in FIG. 1. As shown, a calibration is performed on the first light source 111 and the second light source 112 of the light source device 11 when no any protective glass 100 is placed in the housing 10 and the housing 10 is in the close state, and then the first light intensity value of the first light beam 1110 emitted from the first light source 111 and the second light intensity value of the second light beam 1120 emitted from the second light source 112 are read and recoded (step S1). Next, the movable loading platform 15 is moved out of the housing 10 in response to a press of the measurement start/stop button 14 (step S2). Next, the protective glass 100 to be tested is placed on the movable loading platform 15, the movable loading platform 15 is moved into the housing 10 in response to another press of the measurement start/stop button 14, and the vacuum suction device 16 is automatically turned on so as to fix the protective glass 100 to the movable loading platform 15 (step S3). Next, the first light beam 1110 is emitted from the first light source 111 to the hole-shaped region 110 of the protective glass 100 so as to measure the light transmittance of the hole-shaped region 110 under the first light beam 1110, and the aforementioned obtained light transmittance is displayed by the display apparatus 17 (step S4). Next, the first light source 111 is switched by the second light source 112 through the rotation mechanism 113, the second light beam 1120 is emitted from the second light source 112 to the hole-shaped region 110 of the protective glass 100 so as to measure the light transmittance of the hole-shaped region 110 under the second light beam 1120, and the aforementioned obtained light transmittance is displayed by the display apparatus 17 (step S5). Then, an alarm signal is issued from the notice device 18 when the obtained light transmittances of the hole-shaped region 110 under the first light beam 1110 and the second light beam 1120 are not qualified (step S6).

Figure 4:
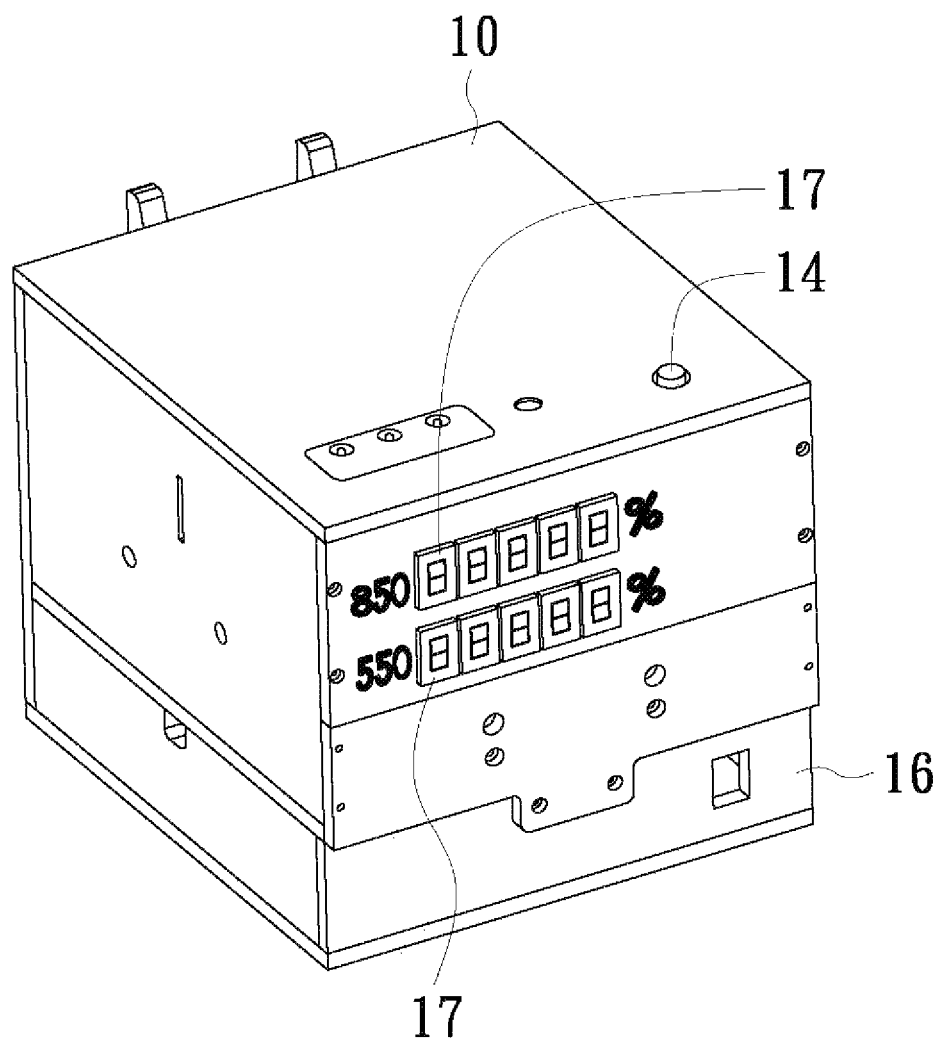
FIG. 4 is a schematic appearance view of the light transmittance measuring apparatus shown in FIG. 1.
Figure 5:
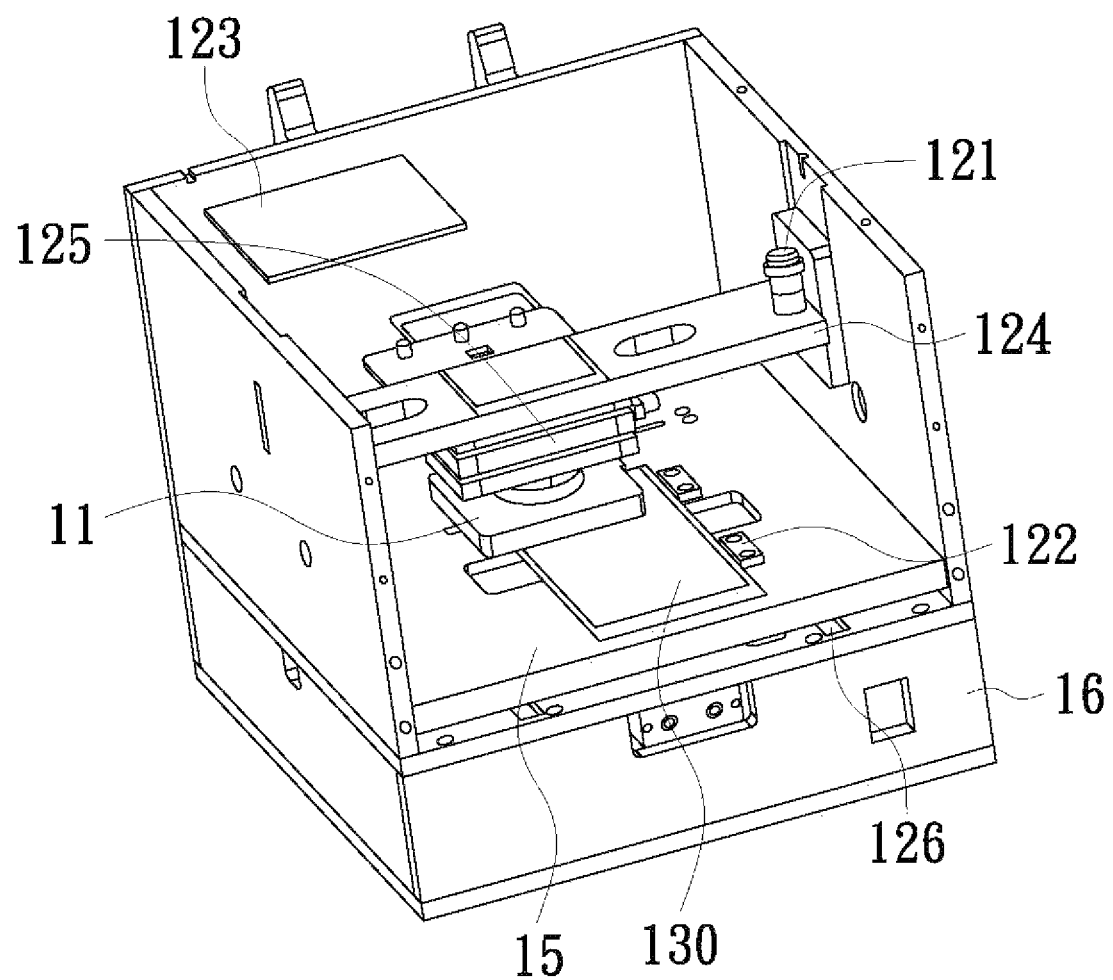
FIG. 5 is a schematic internal structural view of the light transmittance measuring apparatus shown in FIG. 1.
Figure 6:
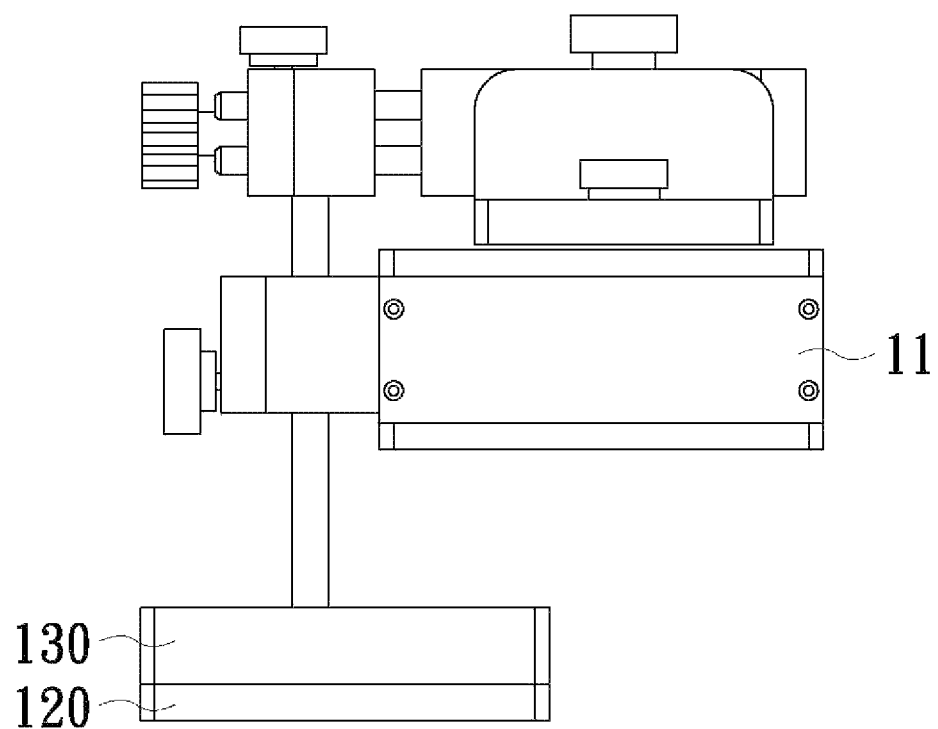
FIG. 6 is a schematic side view of a portion of the internal structure of the light transmittance measuring apparatus shown in FIG. 1.
Figure 7:
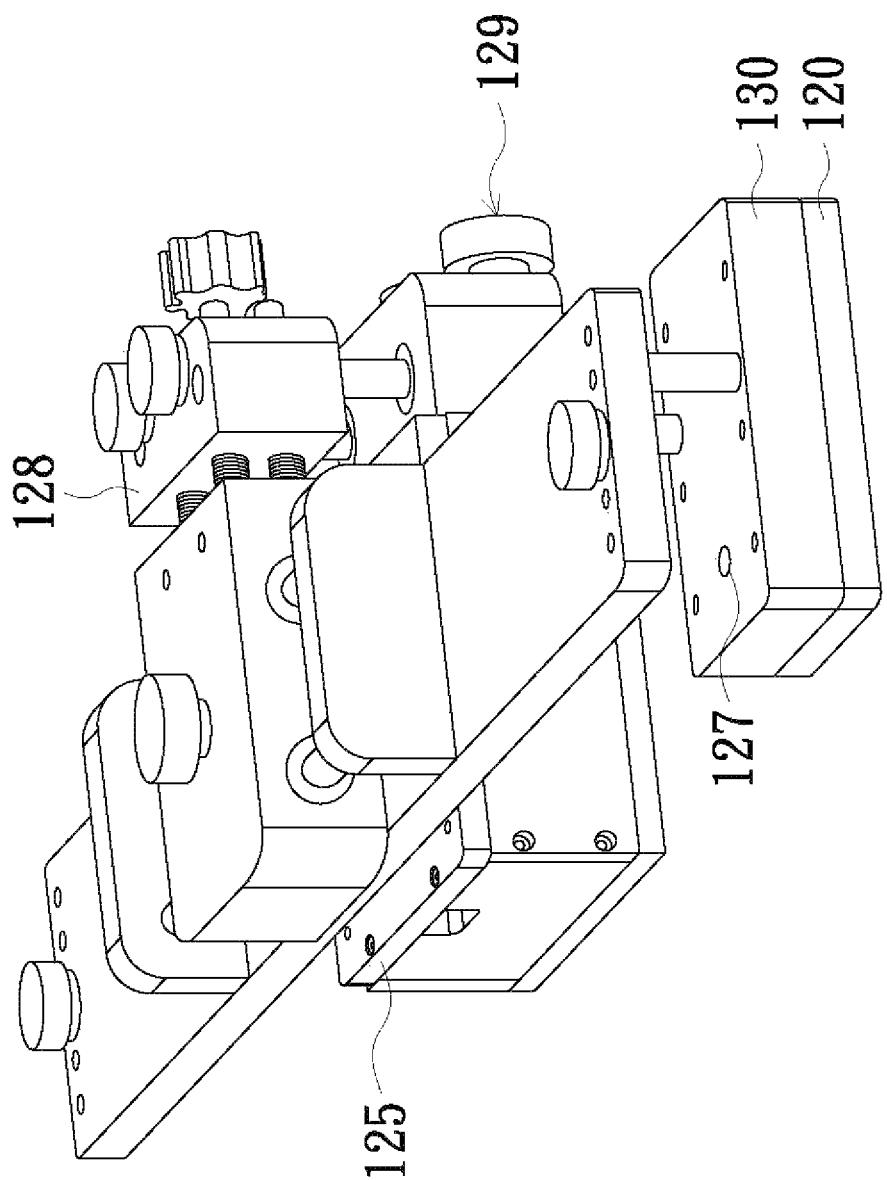
FIG. 7 is a schematic three-dimensional view of the structure shown in FIG. 6.

FIG. 4 is a schematic appearance view of the light transmittance measuring apparatus shown in FIG. 1. As shown, the light transmittance measuring apparatus is mainly assembled by the housing 10 which is made of opaque material. The housing 10 is disposed with the measurement start/stop button 14 and the display apparatus 17 on a surface thereof. FIG. 5 is a schematic internal structural view of the light transmittance measuring apparatus shown in FIG. 1. As shown, the light transmittance measuring apparatus may further include a height adjustment knob 121, a stop-and-adjustment block 122, a test main-board platform 123, a frame transom 124, a rotating cylinder module 125 and a slide rail 126. The height adjustment knob 121 is configured to adjust the height of the frame transom 124. Because the light source device 11 is fixed to the frame transom 124, the height of the light source device 11 is simultaneously adjusted while the height of the frame transom 124 is adjusted through the height adjustment knob 121. The stop-and-adjustment block 122 is disposed on the movable loading platform 15 and configured to fix the protective glass 100 (or other objects to be tested, FIG. 1). The test main-board platform 123 is configured to support the main board of the microcontroller 13 (FIG. 1). The rotating cylinder module 125 is configured to drive the rotation mechanism 113 (FIG. 1) so as to switch the positions of the first light source 111 and the second light source 112 (FIG. 1). The slide rail 126 is configured to move the movable loading platform 15 thereon. FIG. 6 is a schematic side view of a portion of the internal structure of the light transmittance measuring apparatus shown in FIG. 1; and FIG. 7 is a schematic three-dimensional view of the structure shown in FIG. 6. As shown in FIGS. 6 and 7, the light transmittance measuring apparatus may further include a hole-structural modular platform 130 and a light sensor mounting plate 120 disposed under the hole-structural modular platform 130. The light sensor 12 (FIG. 1) is disposed in the light sensor mounting plate 120. The hole-structural modular platform 130 is embedded in the movable loading platform 15 (FIG. 1) and has a hole structure 127; wherein the hole-shaped region 110 of the protective glass 100 (FIG. 1) is aligned to the hole structure 127 when the protective glass 100 (FIG. 1) is placed on the movable loading platform 15 (FIG. 1). In addition, as shown in FIG. 7, the light transmittance measuring apparatus may further include a position adjustment module 128 and an air inlet 129. The position adjustment module 128 is configured to adjust the vertical positions of the rotating cylinder module 125 and the light source device 11 (FIG. 1) through a guide pillar and a fastening bolt (not shown), and consequentially the relative positions between the object to be tested and the rotating cylinder module 125 as well as the light source device 11 are adjusted. In one embodiment, because the rotating cylinder module 125 is a pneumatic device, air can be delivered to a control valve (not shown) in the light transmittance measuring apparatus through the air inlet 129.

In summary, the light transmittance measuring apparatus of the present invention at least has the following characteristics and advantages:

1. Elimination of ambient light interference and improved measuring accuracy. Because the external ambient light can be completely blocked by the housing in close state, the interference of the ambient light on the object to be tested is efficiently reduced. Thus, the light transmittance measuring apparatus of the present invention has higher measuring accuracy.

2. Measurement of two different light sources can be completed in one measuring process. Because the light source device is able to sequentially emit two light beams with different wavelength ranges and the rotation mechanism is able to switch the two light beams, the measurement of the two different light beams can be completed by one light transmittance measuring apparatus of the present invention.

3. Shorter test time and higher production efficiency. Because the measuring process, from the object to be tested is placed on the movable loading platform to the measuring result is obtained, is automatically controlled by the microcontroller, the measuring time is shorter and an operator can handle more than one light transmittance measuring apparatus of the present invention at the same time. Thus, the light transmittance measuring apparatus of the present invention has higher efficiency and improved production performance.

4. Modular design and higher compatibility. When the light transmittance measuring apparatus is used for other types of object or other light sources with specific wavelength ranges, only the light source device and the movable loading platform are needed to be changed due to both have the modular design feature. Thus, the light transmittance measuring apparatus of the present invention has a higher compatibility.

While the invention has been described in terms of what is presently considered to be the most practical and preferred embodiments, it is to be understood that the invention needs not be limited to the disclosed embodiment. On the contrary, it is intended to cover various modifications and similar arrangements included within the spirit and scope of the appended claims which are to be accorded with the broadest interpretation so as to encompass all such modifications and similar structures.

What is claimed is:

1. A light transmittance measuring apparatus used to measure a light transmittance of an object, the light transmittance measuring apparatus comprising:
   a housing, made of an opaque material;
   a light source device, disposed in the housing and configured to emit a first light beam and a second light beam to the object, wherein the first light beam and the second light beam have different wavelength ranges and have a first light intensity value and a second light intensity value, respectively;
   a light sensor, disposed in the housing and configured to sense the first light beam and the second light beam after passing through the object and accordingly obtain a third light intensity value and a fourth light intensity value, respectively;
   a movable loading platform disposed in the housing and configured to move between the light source device and the light sensor to perform a position modulation operation for the object on the movable loading platform; and
   a microcontroller, disposed in the housing and electrically connected to the movable loading platform, the light source device and the light sensor, the microcontroller being configured to compare the first and third light intensity values and accordingly obtain the light transmittance of the object under the first light beam and compare the second and fourth light intensity values and accordingly obtain the light transmittance of the object under the second light beam.

2. The light transmittance measuring apparatus according to claim 1, further comprising a measurement start/stop button disposed on the housing and electrically connected to the microcontroller, the measurement start/stop button being configured to generate a measurement start signal in response to a press of the measurement start/stop button when the housing is in an open state, wherein the microcontroller is further configured to switch the housing from the open state to a close state and control the light source device to sequentially emit the first and second light beams to the object in response to the measurement start signal.

3. The light transmittance measuring apparatus according to claim 2, wherein the light source device comprises:
   a first light source, configured to emit the first light beam;
   a second light source, configured to emit the second light beam; and
   a rotation mechanism, electrically connected to the microcontroller and comprising a rotation part, a first connection part and a second connection part, wherein the first and second connection parts both are connected to the rotation part, the rotation mechanism is connected to the first and second light sources through the first and second connection parts, respectively, wherein the microcontroller is further configured to control the rotation part to rotate in response to the measurement start signal and thereby the first and second connection parts drive the first and second light sources to perform a position switch, respectively.

4. The light transmittance measuring apparatus according to claim 2, wherein the microcontroller is further configured to control the movable loading platform to move between to the light source device and the light sensor in response to the measurement start signal.

5. The light transmittance measuring apparatus according to claim 4, wherein the microcontroller is further configured to control the movable loading platform to perform the position modulation operation when the movable loading platform is moved between to the light source device and the light sensor and the housing is in the close state.

6. The light transmittance measuring apparatus according to claim 4, wherein the measurement start/stop button is further configured to generate a measurement stop signal in response to a press of the measurement start/stop button when the housing is in the close state, wherein the microcontroller is further configured to move the movable loading platform out of the housing in response to the measurement stop signal and thereby switch the housing from the close state to the open state.

7. The light transmittance measuring apparatus according to claim 4, further comprising a vacuum suction device disposed in the housing and electrically connected to the microcontroller, wherein the microcontroller is further configured to control the vacuum suction device to generate an air flow in the housing in response to the measurement start signal and thereby form a negative pressure to fix the object to the movable loading platform.

8. The light transmittance measuring apparatus according to claim 1, further comprising a display apparatus disposed on the housing and electrically connected to the microcontroller, wherein the display apparatus is configured to show the light transmittances, obtained by the microcontroller, of the object under the first and second light beams.

9. The light transmittance measuring apparatus according to claim 8, wherein the display apparatus comprises a numeral tube.

10. The light transmittance measuring apparatus according to claim 1, further comprising a notice device disposed on the housing and electrically connected to the microcontroller, wherein the microcontroller is further configured to control the notice device to issue an alarm signal when the obtained light transmittances of the object under first and second light beams are not qualified.

11. The light transmittance measuring apparatus according to claim 10, wherein the notice device comprises an indicator light or a buzzer.

12. The light transmittance measuring apparatus according to claim 1, wherein the first light beam is a green light having a wavelength range from 495 nm to 570 nm, and the second light beam is a near-infrared light having a wavelength range from 750 nm to 1400 nm.

13. The light transmittance measuring apparatus according to claim 1, wherein the object is a protective glass comprising at least one hole-shaped region, the first and second light beams emitted from the light source device are configured to sequentially pass through the at least one hole-shaped region of the protective glass.

14. The light transmittance measuring apparatus according to claim 1, wherein the light sensor further obtains the first light intensity value and the second light intensity value under the circumstance that no object is placed in the housing and the housing is in a close state.

15. The light transmittance measuring apparatus according to claim 1, further comprising a height adjustment knob and a frame transom, wherein the light source device is fixed to the frame transom, and the height adjustment knob is configured to adjust the height of the frame transom, and wherein the height of the light source device is simultaneously adjusted while the height of the frame transom is adjusted through the height adjustment knob.

16. The light transmittance measuring apparatus according to claim 1, further comprising a stop-and-adjustment block disposed on the movable loading platform and configured to fix the position of the object on the movable loading platform.

17. The light transmittance measuring apparatus according to claim 1, further comprising a test main-board platform configured to support a main board of the microcontroller.

18. The light transmittance measuring apparatus according to claim 1, further comprising a rotating cylinder module configured to drive the rotation mechanism.

19. The light transmittance measuring apparatus according to claim 1, further comprising a slide rail configured to move the movable loading platform thereon.

20. The light transmittance measuring apparatus according to claim 1, wherein the light transmittance of the object is obtained by the equation: $T=(I_{OUT}/I_{IN})\times 100\%$; where $I_{IN}$ is the light intensity value of an incident light before passing through the object, and $I_{OUT}$ is the light intensity value of the incident light after passing through the object.

* * * * *